(12) United States Patent
Kim et al.

(10) Patent No.: US 9,498,243 B2
(45) Date of Patent: Nov. 22, 2016

(54) HANDPIECE

(71) Applicant: YONSEI UNIVERSITY WONJU INDUSTRY-ACADEMIC COOPERATION FOUNDATION, Gangwon-do (KR)

(72) Inventors: Yang-soo Kim, Gwangmyeong-si (KR); Won-ky Kim, Wonju-si (KR)

(73) Assignee: Yonsei University Wonju Industry-Academic Cooperation Foundation, Wonju-si (KR)

( * ) Notice: Subject to any disclaimer, the term of this patent is extended or adjusted under 35 U.S.C. 154(b) by 100 days.

(21) Appl. No.: 14/371,666

(22) PCT Filed: Jan. 8, 2013

(86) PCT No.: PCT/KR2013/000111
§ 371 (c)(1),
(2) Date: Jul. 10, 2014

(87) PCT Pub. No.: WO2013/105762
PCT Pub. Date: Jul. 18, 2013

(65) Prior Publication Data
US 2014/0343589 A1 Nov. 20, 2014

(30) Foreign Application Priority Data
Jan. 12, 2012 (KR) ........................ 10-2012-0003895

(51) Int. Cl.
*A61B 17/32* (2006.01)
*A61B 17/16* (2006.01)
*A61B 17/00* (2006.01)

(52) U.S. Cl.
CPC ............ *A61B 17/32* (2013.01); *A61B 17/1622* (2013.01); *A61B 2017/00017* (2013.01); *A61B 2017/00544* (2013.01)

(58) Field of Classification Search
CPC .............. A61B 17/32; A61B 17/1622; A61B 2017/00017; A61B 2017/00544
See application file for complete search history.

(56) References Cited

U.S. PATENT DOCUMENTS 8,388,879 B2     3/2013  Kim et al.
2006/0286505 A1* 12/2006  Kawakubo ........... A61C 1/0038
                                                433/132

FOREIGN PATENT DOCUMENTS

| JP | 6-98898 A | 4/1994 |
|---|---|---|
| JP | 2003-019114 A | 1/2003 |
| JP | 3125885 U | 10/2006 |
| JP | 4160319 B2 | 10/2008 |
| KR | 10-2006-0131636 | 12/2006 |

OTHER PUBLICATIONS

International Search Report of PCT/KR2013/000111 dated Apr. 15, 2013; 2 pages.

* cited by examiner

*Primary Examiner* — Ashley Fishback
(74) *Attorney, Agent, or Firm* — Daly, Crowley, Mofford & Durkee, LLP

(57) ABSTRACT

A hand piece includes a main body, an impeller, an air supplier, an exhauster and an exhaust controller. The impeller is received by the main body and is rotated in the main body. The air supplier is disposed at the main body and supplies an air to the impeller. The exhauster is disposed at the main body and exhausts the air supplied to the impeller. The exhaust controller is inserted into the exhauster and controls the exhaust of the air based on an air pressure exhausted from the exhauster.

6 Claims, 2 Drawing Sheets

100

HANDPIECE

PRIORITY STATEMENT

This application is the U.S. National Stage of application PCT/KR2013/000111 having an International Filing Date of Jan. 8, 2013, which claims priority to and the benefit of Korean Patent Application No. 10-2012-0003895, filed on Jan. 12, 2012 in the Korean Intellectual Property Office (KIPO), the contents of which application are herein incorporated by reference in their entirety.

BACKGROUND

1. Field of Disclosure

The present disclosure of invention relates to a hand piece. More particularly, the present disclosure of invention relates to a hand piece used for a medical treatment.

2. Description of Related Technology

Generally, in an air-driven hand piece used for a medical treatment, a pressurized air is provided to an impeller received by a head of the hand piece and thus a cutting tool fixed at the impeller is rotated.

In the hand piece, an air flow due to the rotation of the impeller generates pressure difference between an inside of the head and an outside of the head, and this a sound pressure is generated in the head whenever the pressurized air stops being provided. Here, foreign substance or impurities may be inhaled into the head through a gap between the head and the cutting tool, and it is called as "Suck Back".

The impurities may be stacked in the hand piece due to the Suck Back, and the impurities may be exposed to the patient so that the patient may be infected by the hand piece. Thus, various kinds of hand pieces have been developed to prevent the Suck Back. However, the head of the hand piece is limited in the space and the structure, and thus the hand piece for preventing the Suck Back is hard to be designed within the head of the hand piece.

SUMMARY

The present invention provides a hand piece capable of preventing the Suck Back more efficiently.

According to an example embodiment, a hand piece includes a main body, an impeller, an air supplier, an exhauster and an exhaust controller. The impeller is received by the main body and is rotated in the main body. The air supplier is disposed at the main body and supplies an air to the impeller. The exhauster is disposed at the main body and exhausts the air supplied to the impeller. The exhaust controller is inserted into the exhauster and controls the exhaust of the air based on an air pressure exhausted from the exhauster.

In an example embodiment, the exhaust controller may include an exhaust pipe connected to the exhauster and having exhaust holes through which the air is exhausted, a piston inserted into the exhaust pipe, and an elastic member controlling the movement of the piston.

In an example embodiment, the elastic member may be pressed by an exhausting force of the air when the air is supplied to the impeller, and may be released when the air stops being supplied to the impeller.

In an example embodiment, the piston may open or close the exhaust holes according to pressing or releasing of the elastic member.

In an example embodiment, the elastic member may be a spring.

In an example embodiment, the exhaust controller may be detachable to the exhauster.

In an example embodiment, the exhaust controller may further include an O-ring sticking the exhauster to the exhaust pipe.

According to the present example embodiments, the exhaust controller is formed at the exhauster of the hand piece, and thus the piston opens the exhaust holes to exhaust the air when the pressurized air is supplied to the exhauster and the piston closes the exhaust holes to block the exhaust of the air when the pressurized air stops being supplied. Thus, a sound pressure may be prevented from being generated in the main body of the hand piece, and the Suck Back may be effectively prevented.

In addition, the hand piece may be more simplified and optimally designed, and the exhaust controller may be properly used because the exhaust controller is detachable to the hand piece.

BRIEF DESCRIPTION OF THE DRAWINGS

The above and other features and advantages will become more apparent by describing exemplary embodiments thereof with reference to the accompanying drawings, in which.

DETAILED DESCRIPTION

Hereinafter, exemplary embodiment of the invention will be explained in detail with reference to the accompanying drawings.

Figure 1:
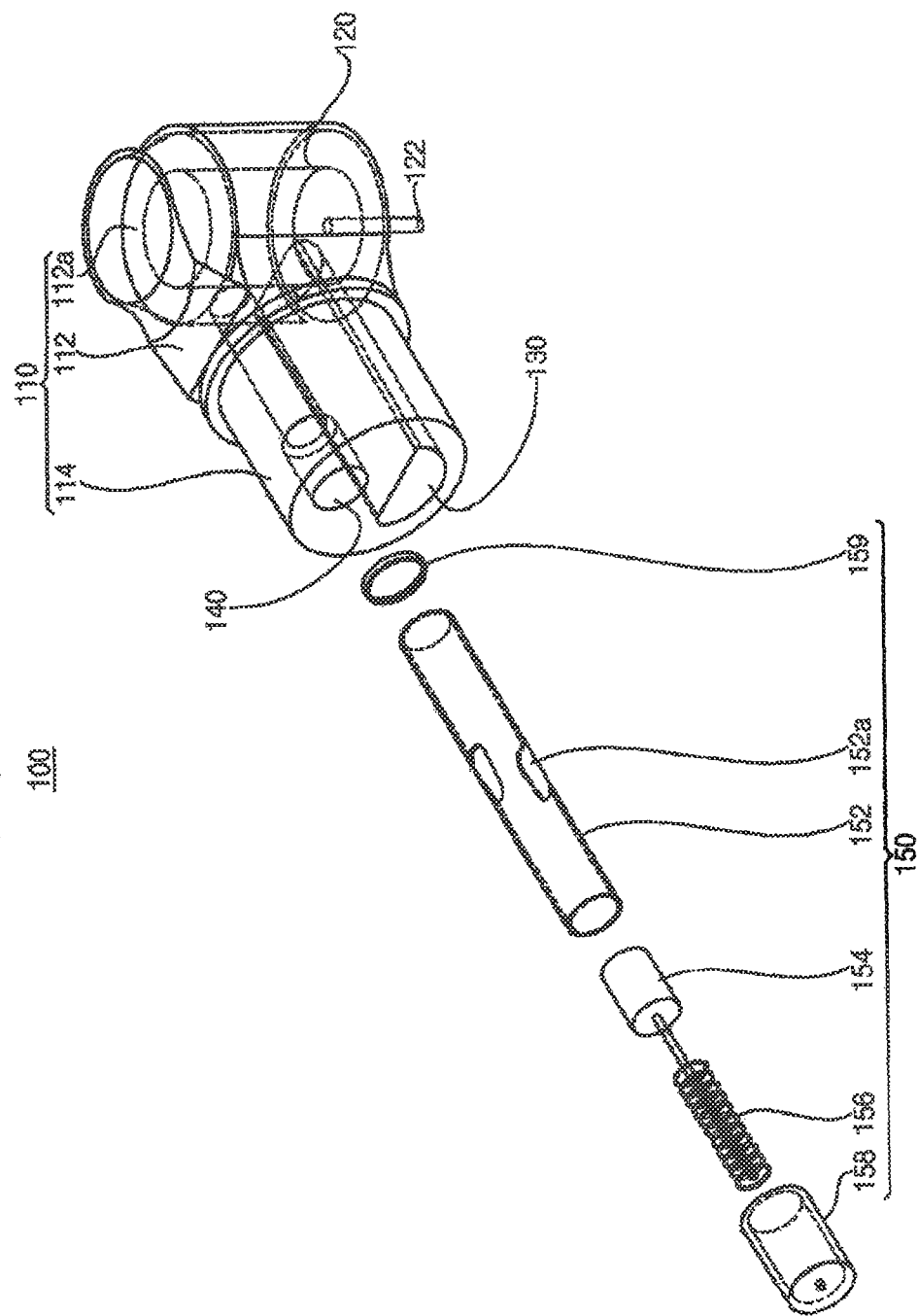
FIG. 1 is an exploded perspective view illustrating a hand piece according to the present example embodiment of the invention.

FIG. 1 is an exploded perspective view illustrating a hand piece according to the present example embodiment of the invention.

Referring to FIG. 1, the hand piece 100 according to the present example embodiment includes a main body 110, an impeller 120, an air supplier 130, an exhauster 140 and an exhaust controller 150.

The main body 110 includes a head portion 112 and a grip portion 114. The impeller is mounted in the head portion 112, and an operator grips the grip portion 114 in treating the patient. The main body 110 forms a receiving space 112a in which the impeller 120 is received. The air supplier 130 and the exhauster 140 are formed through the main body 110.

The main body 110 may have various kinds of shapes, and not limited to FIG. 1, and thus may be designed based on the kinds of treatment by the operator and so on. For example, the head portion 112 may be smaller than the grip portion 114.

The impeller 120 is received in the main body 110 and is rotated in the main body 110. For example, the impeller 120 is received in the receiving space 112a of the head portion 112. The impeller 120 rotates along a direction using the pressurized air supplied from the air supplier 130, and transmits the rotational force to a cutting tool 122 connected to the impeller 120. The impeller 120 has a structure generating the rotational force based on the pressurized air.

The air supplier 130 is formed from an outside of the main body 110 to the receiving space 112a. The air supplier 130 is a pathway through which the pressurized air is supplied to the receiving space 112a.

The exhauster 140 is also formed from the outside of the main body 110 to the receiving space 112a like the air supplier 130. The exhauster 140 is a pathway through which the pressurized air supplied to the receiving space 112a is exhausted, and is spaced apart from the air supplier 130. Accordingly, the pressurized air supplied through the air supplier 130 provides the rotational force to the impeller 120 and is exhausted through the exhauster 140.

The exhaust controller 150 is inserted into the exhauster 140 and controls the air exhausting from the exhauster 140. For example, the exhaust controller 150 includes an exhaust pipe 152, a piston 154, an elastic member 156 and a cover portion 158.

The exhaust pipe 152 has a diameter enough to be tightly inserted to the exhauster 140, and has a pipe shape with a constant length. The exhaust pipe 152 includes a plurality of exhaust holes 152a formed through a sidewall of the exhaust pipe 152 to exhaust the air of the exhaust pipe 152.

The piston 154 has a diameter enough to be tightly inserted to the exhaust pipe 152 and is inserted into the exhaust pipe 152. Thus, the air inside of the pipe 152 is blocked by the piston 154 and is only exhausted to an outside of the exhaust pipe 152 through the exhaust holes 152a.

The elastic member 156 is disposed at a side of the piston 154. For example, the elastic member 156 is disposed at the side of the piston 145 opposite to the exhauster 140. Thus, the elastic member 156 is released when the piston 154 is close to the exhauster 140, and is pressed when the piston 154 is away from the exhauster 140. The elastic member 156 may include a spring. Alternatively, the elastic member 156 may include any members having the elasticity.

The exhaust controller 150 may further include a cover portion 158 fixing a side of the exhaust pipe 152. The cover portion 158 is fixed at an end portion of the exhaust pipe 152 which is not inserted into the exhauster 140, and fixes the end portion of the spring 156.

The exhaust holes 152a formed through the exhaust pipe 152 is closed by the piston 154 when the elastic member 156 is released, and is open by the piston 154 when the elastic member 156 is pressed. Basically, the piston 154 is positioned to close the exhaust holes 152a when the hand piece 100 is initially positioned.

The elastic member 156 has an elastic coefficient such that the elastic member 156 is pressed when the air exhausted from the exhauster 140 has a predetermined pressure. For example, the elastic member 156 has an elastic coefficient such that the elastic member 156 is pressed by the exhausting air when the pressurized air generally operating the hand piece 100 is supplied from the air supplier 130 and is exhausted to the exhauster 140. Thus, the elastic member 156 is pressed when the hand piece 100 is generally driven, and the piston 154 is positioned to open the exhaust holes 152a. However, the elastic member 156 has the elastic coefficient such that the elastic member 156 is released when the pressurized air stops to be supplied to the exhauster 130. Thus, the elastic member 156 is released when the hand piece 100 stops driving, and the piston 154 is positioned to close the exhaust holes 152a. The operation of the exhaust controller 150 will be explained below referring to FIGS. 2A and 2B.

The exhaust controller 150 may further include an O-ring 159 to prevent the air from leaking between the exhaust pipe 152 and the exhauster 140. The O-ring 159 may stick the exhauster 140 to the exhaust pipe 152 to prevent the air from leaking when the exhaust pipe 152 is inserted into the exhauster 140.

The exhaust controller 150 is detachable to the exhauster 140. Thus, the exhaust controller 150 may be attached or detached to the exhauster 140 based on the kind of treatments for the patient. Alternatively, although not shown in the figure, the exhaust controller 150 may be fixed to the exhauster 140.

As explained above, in the hand piece according to the present example embodiment, the piston of the exhaust controller opens the exhaust holes to exhaust the air when the pressurized air is provided, and the piston closes the exhaust holes to stop exhausting the air when the pressurized air is not supplied. Thus, the air stops being exhausted when the pressurized air is not supplied, and thus the sound pressure of the main body may be prevented. Accordingly, the Suck Back may be prevented more efficiently.

In addition, an additional exhaust controller is not disposed in the main body of the hand piece, and thus the hand piece may have more simplified structure and may be minimized.

In addition, when the additional exhaust controller is disposed in the main body, the exhaust controller may be dropped in efficiency due to a repeated sterilization of the hand piece. However, the hand piece according to the present example embodiment may be easily detachable, and the hand piece may be easily sterilized, repaired or exchanged.

Figure 2A:
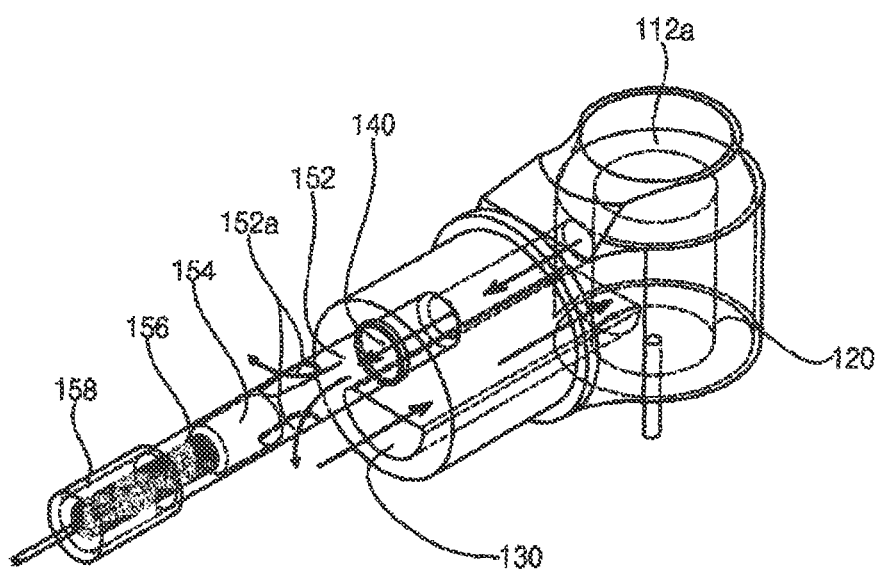
FIGS. 2A and 2B are conceptual views illustrating an operation of an exhaust controller in FIG. 1.
Figure 2B:
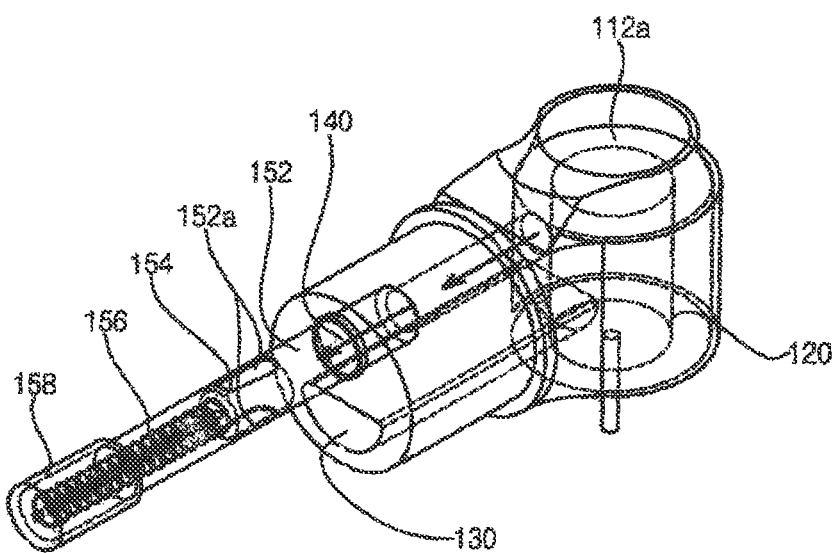

FIGS. 2A and 2B are conceptual views illustrating an operation of an exhaust controller in FIG. 1.

Referring to FIGS. 1 and 2A, when the hand piece 100 is operated, for example, the pressurized air is supplied from the air supplier 130 and is exhausted through the exhauster 140, the air exhausted from the exhauster 140 is inhaled to the exhaust pipe 152 of the exhaust controller 150 inserted into the exhauster 140. The air injected into the exhaust pipe 152 pushes the piston 154 due to the pressure of the pressurized air continuously supplied from the air supplier 130, and thus the elastic member 156 is pressed. Here, the piston 154 opens the exhaust holes 152a of the exhaust pipe 152, and the air injected into the exhaust pipe 152 is exhausted to outside through the exhaust holes 152a. Accordingly, when the hand piece 100 operates, the pressurized air is circulated in the main body 110.

Referring to FIGS. 1 and 2B, when the hand piece 100 stops operating, for example, the pressurized air stops being supplied from the air supplier 130, the air exhausting from the exhauster 140 does not receive the pressure from the pressurized air and thus the pressure for pushing the piston 154 is not maintained. Thus, the elastic member 156 pushes the piston 154 and the piston 154 returns to the initial position, and thus the exhaust holes 152a of the exhauster are closed. Here, the air inside of the hand piece 100 is not exhausted to outside any more, and the sound pressure of the hand piece 100 is prevented from being generated. Thus, the Suck Back due to the sound pressure of the hand piece 100 is instantly prevented from being generated.

According to the present invention, the exhaust controller is formed at the exhauster of the hand piece, and thus the piston opens the exhaust holes to exhaust the air when the pressurized air is supplied to the exhauster and the piston closes the exhaust holes to block the exhaust of the air when the pressurized air stops being supplied. Thus, a sound pressure may be prevented from being generated in the main body of the hand piece, and the Suck Back may be effectively prevented.

In addition, the hand piece may be more simplified and optimally designed, and the exhaust controller may be properly used because the exhaust controller is detachable to the hand piece.

The foregoing is illustrative of the present teachings and is not to be construed as limiting thereof. Although a few exemplary embodiments have been described, those skilled in the art will readily appreciate from the foregoing that many modifications are possible in the exemplary embodiments without materially departing from the novel teachings and advantages of the present disclosure of invention. Accordingly, all such modifications are intended to be included within the scope of the present teachings. In the claims, means-plus-function clauses are intended to cover the structures described herein as performing the recited function and not only structural equivalents but also functionally equivalent structures.

What is claimed is:

1. A hand piece comprising:
    a main body;
    an impeller received by the main body and rotated in the main body;
    an air supplier disposed at the main body and supplying air to the impeller;
    an exhauster disposed at the main body and configured to exhaust the air supplied to the impeller; and
    an exhaust controller inserted into the exhauster and controlling the exhaust of the air based on an air pressure exhausted from the exhauster;
    wherein the exhauster controller is detachable to the exhauster.

2. The hand piece of claim 1, wherein the exhaust controller comprises:
    an exhaust pipe connected to the exhauster and having exhaust holes through which the air is exhausted;
    a piston inserted into the exhaust pipe; and
    an elastic member controlling the movement of the piston.

3. The hand piece of claim 2, wherein the elastic member is pressed by an exhausting force of the air when the air is supplied to the impeller, and is released when the air stops being supplied to the impeller.

4. The hand piece of claim 3, wherein the piston opens or closes the exhaust holes according to pressing or releasing of the elastic member.

5. The hand piece of claim 3, wherein the elastic member comprises a spring.

6. The hand piece of claim 2, wherein the exhaust controller further comprises an O-ring sticking the exhauster to the exhaust pipe.

* * * * *